US009200986B1

(12) United States Patent
Mayeaux

(10) Patent No.: US 9,200,986 B1
(45) Date of Patent: Dec. 1, 2015

(54) FLUID SAMPLING PROBE WITH VIBRATION DAMPENING

(71) Applicant: A+ Manufacturing, LLC, Gonzales, LA (US)

(72) Inventor: Donald P Mayeaux, Prarieville, LA (US)

(73) Assignee: A+ Manufacturing, LLC, Gonzales, LA (US)

( * ) Notice: Subject to any disclaimer, the term of this patent is extended or adjusted under 35 U.S.C. 154(b) by 341 days.

(21) Appl. No.: 13/765,561

(22) Filed: Feb. 12, 2013

Related U.S. Application Data

(63) Continuation-in-part of application No. 12/822,920, filed on Jun. 24, 2010, now Pat. No. 8,522,630.

(60) Provisional application No. 61/288,317, filed on Dec. 20, 2009.

(51) Int. Cl.
  *G01D 21/00* (2006.01)
  *G01N 17/00* (2006.01)
  *G01N 1/10* (2006.01)

(52) U.S. Cl.
  CPC ........................................ *G01N 1/10* (2013.01)

(58) Field of Classification Search
  CPC .................................................... G01N 1/10
  USPC ........... 73/866.5, 86, 863.81, 863.82, 863.85, 73/863.86; 422/53
  See application file for complete search history.

(56) References Cited

U.S. PATENT DOCUMENTS

| | | | |
|---|---|---|---|
| 3,174,332 A * | 3/1965 | Echtler, Jr. et al. | 73/86 |
| 4,327,586 A * | 5/1982 | Goddard | 73/866.5 |
| 5,106,580 A | 4/1992 | Mudiam | |
| 5,551,707 A * | 9/1996 | Pauley et al. | 277/654 |
| 6,701,794 B2 | 3/2004 | Mayeaux | |
| 6,827,486 B2 | 12/2004 | Welker | |
| 6,964,517 B2 | 11/2005 | Welker | |
| 7,472,615 B2 | 1/2009 | Mayeaux | |
| 2005/0072253 A1 * | 4/2005 | Scott et al. | 73/866.5 |
| 2005/0223829 A1 * | 10/2005 | Mayeaux | 73/866.5 |
| 2005/0247108 A1 * | 11/2005 | Mayeaux | 73/29.01 |

OTHER PUBLICATIONS

Conax Technologies, Process Analyzer Sample Probe Assembly (SPA).. Bulliten 6066, (C) 2009, pp. 1-4.

* cited by examiner

*Primary Examiner* — Peter Macchiarolo
*Assistant Examiner* — Nathaniel Kolb
(74) *Attorney, Agent, or Firm* — Joseph T Regard, Ltd plc

(57) ABSTRACT

A system for insertion of a probe into a pressurized fluid stream by means of a threaded body formed to engage an elastomeric seal employed to form a fluid barrier thereabout. The present invention contemplates a system which effectively lessens resonance vibration effects and associated damage resulting there from in fluid sampling probes operating in high velocity fluid streams and the like, utilizing mechanical dampening properties associated with its seal(s) and insert(s), forming non-rigid attachment to support the length of the probe in a manner which facilitates resonance absorption and dampening, so as to lessen associated vibration/oscillation in the system. The threaded body forms, in effect, helical strakes to facilitate aerodynamic stabilization and reduce oscillations/vibration, as well as reduce force and deflection caused by high velocity fluid flow passing thereby.

31 Claims, 7 Drawing Sheets

FLUID SAMPLING PROBE WITH VIBRATION DAMPENING

BENEFIT CLAIM

The present application is a continuation-in-part of U.S. Utility patent application Ser. No. 12/822,920 entitled "System for Retrieving a Fluid Sample from a Fluid Sample Source" listing Donald P. Mayeaux as the inventor, filed Jun. 24, 2010, which '920 application claimed the benefit of U.S. Provisional Patent Application Ser. No. 61/288,317 filed Dec. 20, 2009, entitled "System for Retrieving a Fluid Sample from a Fluid Sample Source", also listing Donald P. Mayeaux as inventor.

FIELD OF THE INVENTION

The present invention contemplates a system for insertion of a probe into a pressurized fluid stream by means of a threaded body formed to engage an elastomeric seal employed to form a fluid barrier around a segment of the probe's outer surface.

The present invention also contemplates a system designed to lessen resonance vibration effects in sampling probes as well as well as reducing the associated damage resulting there from, these effects particularly troublesome in fluid sampling probes operating in high velocity fluid streams and the like.

The preferred embodiment of the present invention also provides enhanced mechanical dampening via the design and configuration of the seal and insert, providing non-rigid engagement to support the probe along its length, so as to facilitate absorption or dampening to lessen vibration/oscillation in the system.

Further, in the present invention the outer diameter of the probe length has a profile which provides, in effect, helical strakes, which testing has found to facilitate aerodynamic stabilization and reduce oscillations/vibration, as well as force and deflection caused by high velocity fluid flow passing thereby, while also providing a threaded outer surface for longitudinal positioning of the probe into our out of the fluid stream.

GENERAL BACKGROUND

It is common practice for fluid samples to be extracted from a pressurized pipeline for "on-line" analysis or laboratory analysis. Such is the case in the natural gas industry wherein the monetary value of the gas is dependent on its composition. The chemical and oil refining industries also have needs for extracting fluid samples from pressurized fluid sources.

Additionally sensors, such as pressure and temperature sensors and corrosion coupons often require insertion into pressurized fluid streams. There are many probe types designed to be inserted into pressurized fluid systems. There are pressure balance insertion methods, such as described in Mayeaux U.S. Pat. Nos. 7,472,615 and 6,701,794, which do not require forcing the probe through a seal. There are smooth walled probe types, such as described in Welker U.S. Pat. Nos. 6,964,517 and 6,827,486, which are forced through a seal into a pressurized fluid by pneumatic or hydraulic means. Another probe insertion method utilizes a threaded male membrane and threaded female nut to force a smooth walled probe through a seal into the pressurized fluid. An example is the Mudiam U.S. Pat. No. 5,106,580.

The aforementioned methods of probe insertion each have drawbacks. For example, the Mayeaux patents require a housing with foot valve which prevents it from being utilized in a horizontal position. The Welker patents describe probes requiring valving and pneumatic or hydraulic cylinders which complicates their construction and operation. The Mudiam patent describes a complex apparatus in which a rod type of probe is inserted by utilizing a separate threaded member.

Another common problem associated with the use of sampling probes, sensors or the like in a high velocity fluid stream (or even lower velocity fluid streams, depending upon the structure of the probe and density of the fluid) relates to the phenomenon of resonant vibration induced in the probe itself due to the flow of fluid therethrough.

According to the manual of Petroleum Measurement Standards (API), Chapter 14, Natural Gas Fluids Measurement, Section 1—Collecting and Handling of Natural Gas Samples for Custody Transfer, (Sixth edition, February 2006) (herein referred to as API 14.1 2006) (the contents of which are incorporated herein by reference thereto):

"API 14.1 2006 Section 7.1:

The design must also consider the possibility of resonant vibration being induced in the probe by high flowing velocities in the pipeline.

API 14.1 2006 Section 7.4.1:

It is industry practice that the collection end of the probe be placed within the approximate center one-third of the pipe cross-section. While it is necessary to avoid the area most likely to contain migrating liquids, the pipe wall, it may be necessary to limit the probe length to ensure that it cannot fail due to the effects of resonant vibration.

Resonant vibration can occur when the vortex shedding frequency resulting from a probe inserted into a flowing fluid is equal to or greater than the probe's natural resonant frequency. Table 1 provides recommended probe lengths for typical diameters based on a maximum natural gas velocity of 100 ft/sec (30.48 m/sec)." (Emphasis Ours).

Thus, API recognizes the problem of resonant vibration in probes in high flow environments, and its recommendation is to position the probe away from the pipe wall, as well as "limit the probe length to ensure that it cannot fail due to the effects of resonant vibration", as indicated in the above Section 7.4.1, 1st Para. In fact, Chapter 14 of the above API Standards, Chapter 14, page 14, sets forth recommended maximum probe lengths in an effort to combat resonant vibrations:

TABLE 1

| Maximum Recommended Probe Lengths | |
|---|---|
| Probe Outer Diameter Inches (cm) | Recommended Max Probe Length Inches (cm) |
| 0.25 (0.64) | 2.00 (5.08) |
| 0.375 (0.95) | 3.25 (8.26) |
| 0.50 (1.27) | 4.25 (10.80) |
| 0.75 (1.91) | 6.50 (16.51) |

"Calculations were based on a maximum recommended probe length Strouhal Number of 0.4, a 0.035 in (0.089 cm) wall thickness, and 316 stainless steel probe construction." Further, as indicated by the Gas Processors Association "Obtaining Natural Gas Samples for Analysis by Gas Chromatography Standard 2166 (Rev 2005) (hereinafter referenced as GPA 2166-2005, Section 7.5.2:

"It has been an industry practice that the collection end of the probe be placed within the approximate center one-third of the pipe cross-section. While it is necessary to avoid the area most likely to contain migrating liquids (the pipe wall) it may also be necessary to limit the probe length to ensure that it cannot fail due to the effects of resonant vibration.

Resonant vibration can occur when the vortex shedding frequency resulting from a probe inserted into a flowing fluid is equal to or greater than the probe's natural resonant frequency. Table 2 provides maximum probe lengths for typical diameters based on a maximum natural gas velocity of 100 ft/sec."

TABLE 2

Recommended Maximum Sample Probe Lengths

| Probe Outer Diameter (inches) | Recommended Maximum Probe Length (inches)* |
|---|---|
| 0.250 | 2.00 |
| 0.375 | 3.25 |
| 0.500 | 4.25 |
| 0.750 | 6.50 |

*Calculations were based on a maximum probe length Strouhal Number of 0.4, a 0.035 inch wall thickness, maximum flow velocity of 100 ft. sec. and 316 stainless steel (E = 28,000,000 PSI, r = 7.96 g/cc) probe construction.

Section 7.5.2.1 of the standard specifies specific calculations of the permissible probe length taking into account several criteria including velocity of the fluid, modulus of elasticity of the probe material and its density, and others, and in GPA 2166-2005 Section 7.5.3 it is indicated that:

"Under no circumstances should the Sample Probe be longer than 10".

Caution: Harmonics may cause embrittlement of the metal. Poorly designed Sample Probes may bend or break off in the flowing gas stream."

Many other standards also recognize the inherent problem with current probe designs and the harmonics/resonance issue due to the velocity of fluid flow in the testing area, including ISO 10715:1997, EEMUA 138 (Engineering Equipment and Material Users Assoc) (the contents of which are incorporated herein by reference thereto), and provide guidelines as to appropriate probe length and construction depending upon the sample fluid flow, etc).

One reviewing the above standards would quickly discern that the industry accepted practice for combating resonance and vibration issues in the probe is 1) keep the probe in the central area of the pipe and avoid the pipe walls, as well as to 2) limit the probes length and/or beef up its construction to resist such forces, although both guidelines are limiting by nature and as such basically avoiding the problem instead of responding to it.

One would also note there is no noticeable mention of providing a design profile to lessen vortices and associated vortex shedding-induced vibrations, cavitations, or other disturbances in the fluid flow which can lead to vibrations or oscillation-inducing forces, nor is there mention of providing a means of dampening or absorbing any such forces as an alternative to the structural limitation guidelines summarized above.

Put another way, one may criticize the above industry standards for sampling as it may be construed to limit ones ability to take what may be the best sample likely to contain migrating liquids using a probe in a process pipeline, that is, along the inner pipe wall.

Also, the limitation of probe length recommendations summarized above by the standards commissions are their best efforts at preventing failure of the probes due to the effects of resonant vibration. So the probes, to be compliant, must be long enough to extend into the flowing gas stream and be away from the wall. It has been an industry practice to require the probes to be in the center third of the pipeline. However, another requirement is that the probes can not be longer than 10" in length. Very large diameter pipelines such as 36" or 42" pipelines would require probes longer than the maximum recommended length.

The prior art probes such as described in EEMUA 138 (above) include those which incorporate smooth pieces of tubing welded into fittings. When a fluid flows past a cylindrical projection (smooth tube sample probe) in a pipeline, vortices can form at either side of the cylinder. As the fluid velocity and hence Reynolds Number increases, these vortices tend to grow in size, elongate and eventually detach, first from one side of the smooth cylinder and then from the other. As soon as one vortex detaches, another one can be created. This phenomenon is called "vortex shedding" and the frequency at which it occurs is called the "shed frequency". In developing these vortices the cylinder experiences drag forces in a direction transverse to the fluid flow.

Since the alternate vortices are of opposite signs the cylinder is subject to a periodic transverse force. It has been found experimentally that the typical cylinder wall (which can be in the form of a conventional probe profile) will start to oscillate when the "shed frequency" equals the natural frequency of the cylinder. Also, oscillations tend to continue at velocities beyond the one causing agreement of frequencies up to a maximum of twice the initiating velocity. If such a condition occurs, the smooth tube probe will oscillate and is liable to snap off where the tube is welded into the fitting.

Accordingly, there exists a long felt, but unresolved need in the industry for a sample probe which resists uncontrolled resonant vibrations and associated destructive forces inherent therewith due to contact with the flow of the fluid process stream, said sample probe using an effective and reliable means to control said forces, while not necessarily being subject to the traditional length and structural parameters as set forth in the above industry standards.

GENERAL SUMMARY DISCUSSION OF THE INVENTION

Unlike prior art, smooth shafted probes which are vulnerable to seal failures as well as damages due to uncontrolled resonant vibrations, the present invention incorporates a body having a threaded outer diameter coupled with an effective seal directly engaging said threaded outer diameter, the seal further formed to provide effective mechanical dampening between the probe base and the probe that is inserted into the flowing fluid stream so as to dampen resonant vibration and thereby prevent destructive uncontrolled oscillation thereof.

In the present invention, the probe length of the probe body is supported without rigid points of attachment. Further, the present system incorporates a thermoplastic (Kevlar) female threaded insert (nut) formed to threadingly engage the stainless steel probe threads, which may also further enhance the dampening of resonant vibrations in the system. The use of a thermoplastic insert provides plastic threads which also facilitates a low torque rotation of the stainless steel probe shaft.

The mechanical combination of a dampening seal and a thermoplastic threaded insert may be applicable to other probe designs, including possibly prior art probes, so as to significantly reduce or even possibly eliminate vibration or oscillation problems, especially in high velocity pressurized pipeline applications and more specifically for analytical sample probes. The prior art, smooth tube sample probes may be able to be adapted to utilize the dampening seal and plastic threaded insert construction design of the system of the present invention, and thereby replace the prior art welded fitting portion of those probes.

In addition to a dampening seal, lack of rigid points of attachment, and thermoplastic insert, the present invention also utilizes a threaded member to force a smooth walled rod or probe directly into a pressurized fluid container through a seal, the current invention, as discussed above, and infra, providing an effective seal directly around the threaded area of the threaded member.

Accordingly, the outer diameter of the probe of the preferred embodiment of the present invention is threaded. In the fluid stream, the threaded portion of the probe provides spiral ridges which have been found to function as helical strakes when in contact with the fluid stream, which has been found to effectively act as aerodynamic stabilizers, which can reduce the forces and deflections of the probe due to vortex shedding. Helical strakes in other applications outside of analytical sampling have been used in various iterations, for example, to protect stacks and towers from damage caused by oscillations due to wind induced vortex shedding. In a similar manner, these spiral ridges can act to control, reduce, or even possibly eliminate the formation of the oscillations.

The preferred embodiment of the present invention's concept of providing spiral ridges on the outside diameter of the probe to form vibration dampening helical strakes when exposed to a fluid stream may be adaptable to provide similar relief in prior art (heretofore smooth tube) sample probes as well. In such an adaptation, the spiral ridges do not have to be conventional threads that are used to insert or remove the probe, but rather, may comprise uniquely shaped and non-uniform ridges or the like formed to aerodynamically influence fluid in contact therewith to diminish vortex shedding and the oscillations generated thereby. Also, the present invention may be adapted to provide other surface structures such as knurling or the like for application to prior art smooth tubes to in an effort to reduce the oscillations. This method alone without the dampening could be used to reduce or even eliminate oscillations at some velocities.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein.

DETAILED DISCUSSION OF THE INVENTION

The present invention comprises a probe shaft having external threads which, when rotated, is inserted to or retrieved from a pressurized fluid source through via a threaded seal and a threaded female member. The probe may be configured to extract a fluid sample, insert a sensor or corrosion coupon, or perform a variety of tasks requiring insertion into a pressurized fluid.

Unlike prior art which utilizes a threaded member to force a smooth walled rod or probe into a pressurized fluid container through a seal, the current invention utilizes a seal around the threaded area of the threaded member. This significantly simplifies the construction and reduces the risk of the probe blowing out of the seal.

In addition, the present invention provides the additional benefit of enhanced mechanical dampening via the design and configuration of seals and inserts, providing non-rigid engagement to support the probe along its length, using the packing gland to effectively isolate said probe shaft from the housing by utilizing the material forming the packing gland to effectively absorb or dampen vibration/oscillation in the probe shaft due to engagement of the probe tip with the process gas fluid stream. A threaded insert of thermoplastic or other elastomeric material may also be use in conjunction with the packing gland arrangement to further provide dampening/absorption of harmonic resonance/vibrations in the probe shaft.

Further, the external threads 2 provide an outer profile for the shaft forming, in effect, helical strakes along its length which engage the fluid stream, which testing has found to facilitate aerodynamic stabilization and reduce oscillations/vibration when compared to a smoother OD probe, as well as diminish force and deflection caused by high velocity fluid flow engagement, while also providing a threaded outer surface for longitudinal positioning of the probe into our out of the fluid stream.

Figure 1:
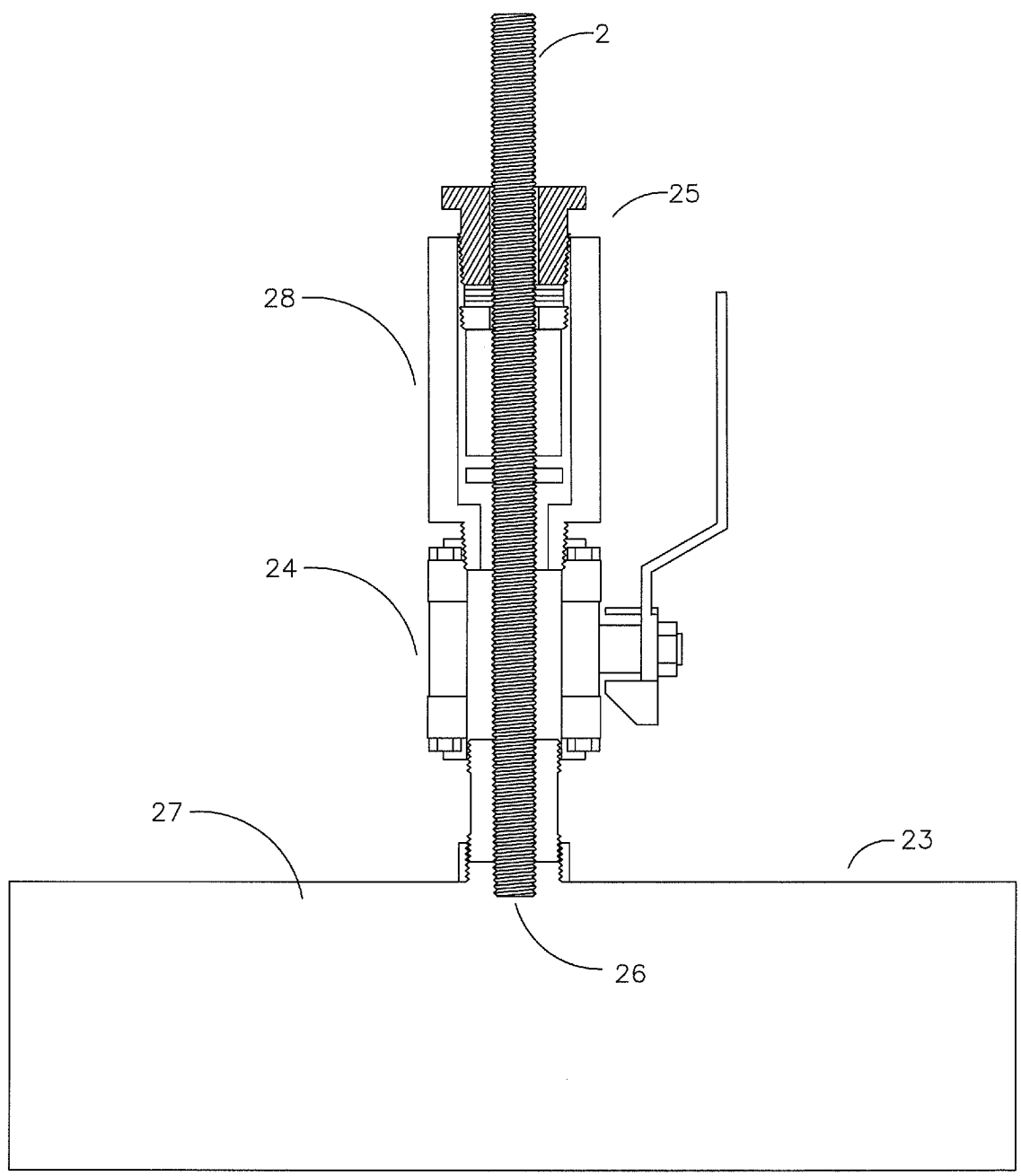
FIG. 1 is a side, partially cut-away view of a preferred embodiment of the insertion assembly of the present invention mounted to a pipeline through an open valve, with a probe tip situated in pressurized fluid.

In the preferred embodiment of the present invention, referring to FIG. 1, insertion assembly 25 is mounted to a pipeline 23 through full opening valve 24 wherein probe tip 26 is located in a pressurized fluid 27.

Figure 2:
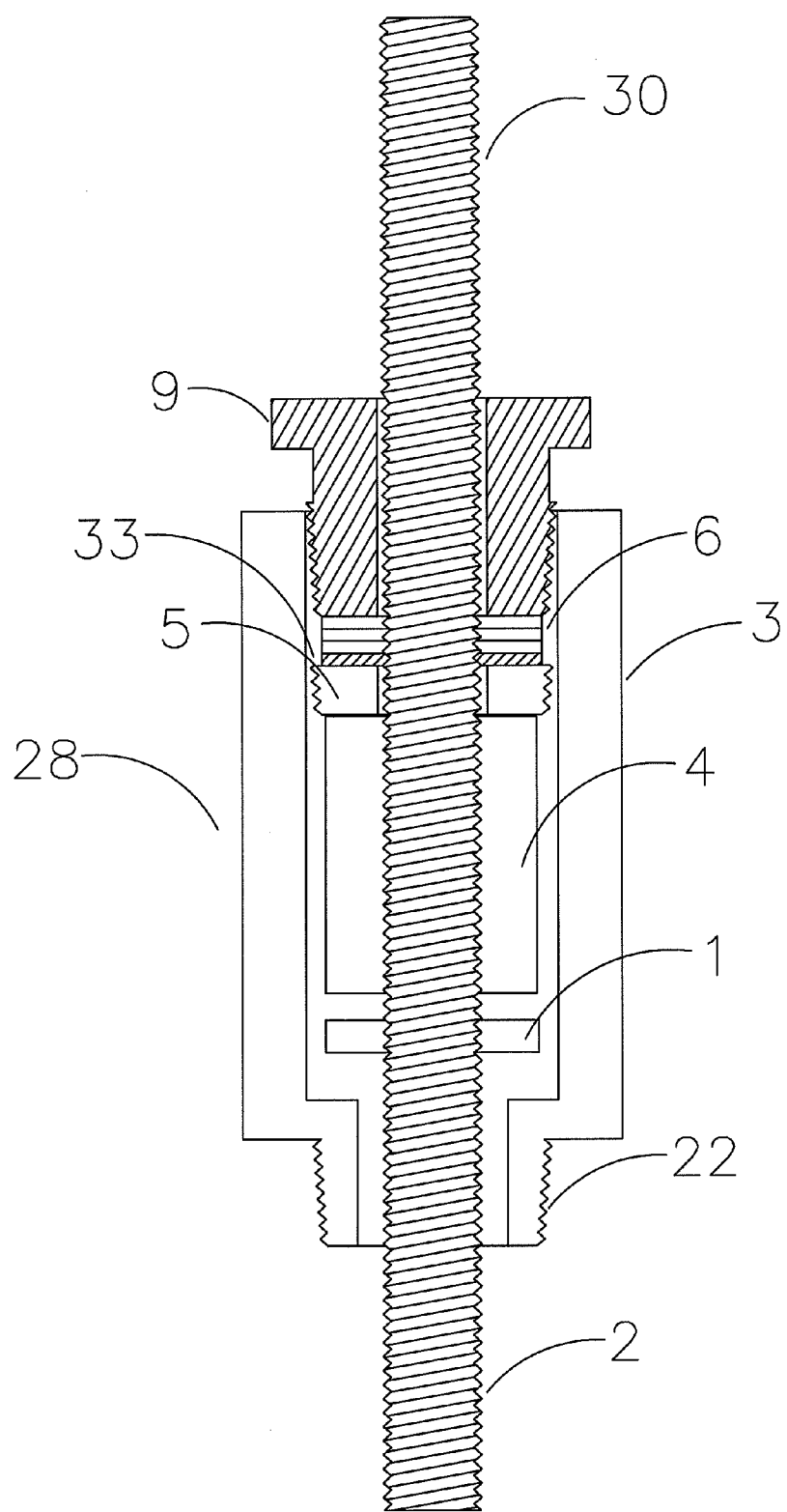
FIG. 2 is a side, partially cut-away view of the invention of FIG. 1, illustrating a closer view of the packing gland, female thread insert, retention nut, and related components.

Housing assembly 28, refer to FIG. 2, consists of housing 3, having an NPT threaded end 22, a thread die or threaded nut 1, female threaded insert 4, insert retention nut 5, packing gland 6, packing gland retention nut 9, and threaded probe shaft 2, having male threads 30.

When insertion assembly 25 is mounted to a pressurized fluid source 27 as shown in FIG. 1 rotating threaded probe shaft 2 (for example, via handle, lever or actuator associated with the probe shaft) will result in said probe shaft 2 being raised or lowered depending on the direction of rotation and thread direction. Female thread insert 4, locked in place by insert retention nut 5, provides the female thread engagement necessary to raise and lower said probe shaft 2 when said probe shaft 2 is rotated.

Figure 7:
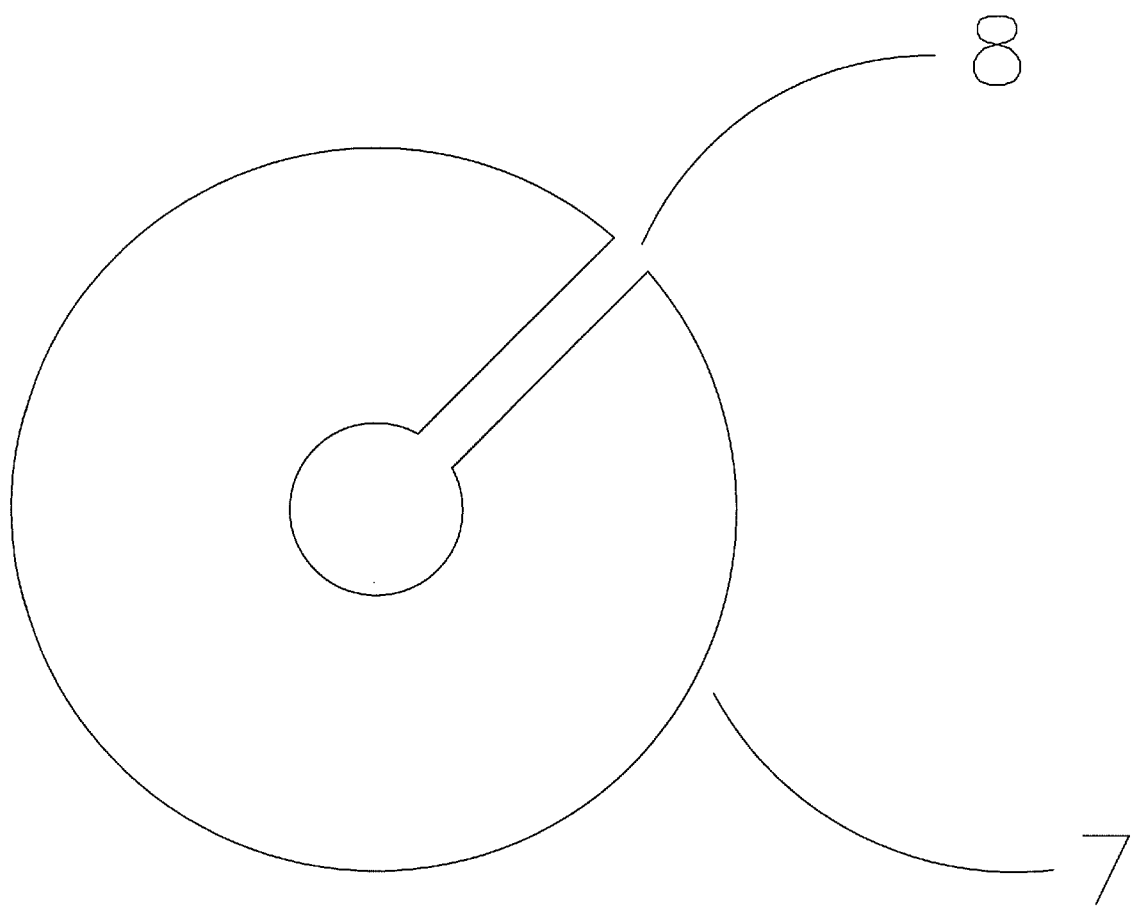
FIG. 7 is a top view illustrating a split disc used to form the packing gland 6 of FIG. 2.

Packing gland 6 is compressed and made to flow tightly around male threads 30 of threaded probe shaft 2 by rotating packing gland retention nut 9. Packing gland 6 as shown in FIG. 2 is constructed of a plurality of single elastomeric split discs 7 which may be slit 8 (Refer to FIG. 7) to accommodate placement around threaded probe shaft 2 after insertion assembly 25 is fully assembled. Refer to FIG. 7. Packing gland 6 may also contain a layer 33, said layer 33 being impervious to a process fluid thereby providing protection against attack of process fluids upon packing gland 6. Packing gland retention nut 9 can be rotated to maintain a leak free fluid seal while insertion assembly 25 is in service.

As shown in the figures, the packing gland, in addition to forming a fluid seal about the outer diameter of the threaded probe shaft and thus directly engaging said probe shaft as well as the inner diameter of housing 3, also provides a dampening media to isolate said probe shaft from housing 3.

Where the packing gland is formed of elastomeric or other vibration absorbing material, this configuration serves, in addition to an effective fluid seal, to isolate the housing from resonant vibrations, oscillations, or the like which might be present in the threaded probe shaft as well as components engaged thereto, was well as providing dampening or absorption of said vibrations, oscillations, or the like via said vibration absorbing material. As shown in FIG. 2, the packing gland 6 effectively suspends and retains the probe shaft 2 within the housing, while isolating same from vibrations originating in the shaft 2 due to the elastomeric or the like material employed in packing gland 6.

One purpose of thread die or threaded nut 1 is to remove scale from the threads as the probe is retracted should said scale accumulate while the probe is exposed to a process fluid. Female thread insert 4 is preferably constructed of a plastic material such as Kevlar. The plastic mass of the threaded insert (as shown in FIG. 2, for example) has been found to absorb resonant vibratory energy or the like emanating from the threaded shaft, while the plastic threads formed through the female thread insert 4 also provides for smooth, low torque rotation of probe shaft 2, said probe shaft 2 is preferably construction of stainless steel.

Threaded die or threaded nut 1 can be used to provide a measure of protection against ejection of probe shaft 2 in the event that housing assembly 28 is installed in a pressurized fluid system having a fluid pressure substantially higher than the pressure rating of said housing assembly 28 resulting in the stripping of threads in female threaded insert 4.

Figure 3:
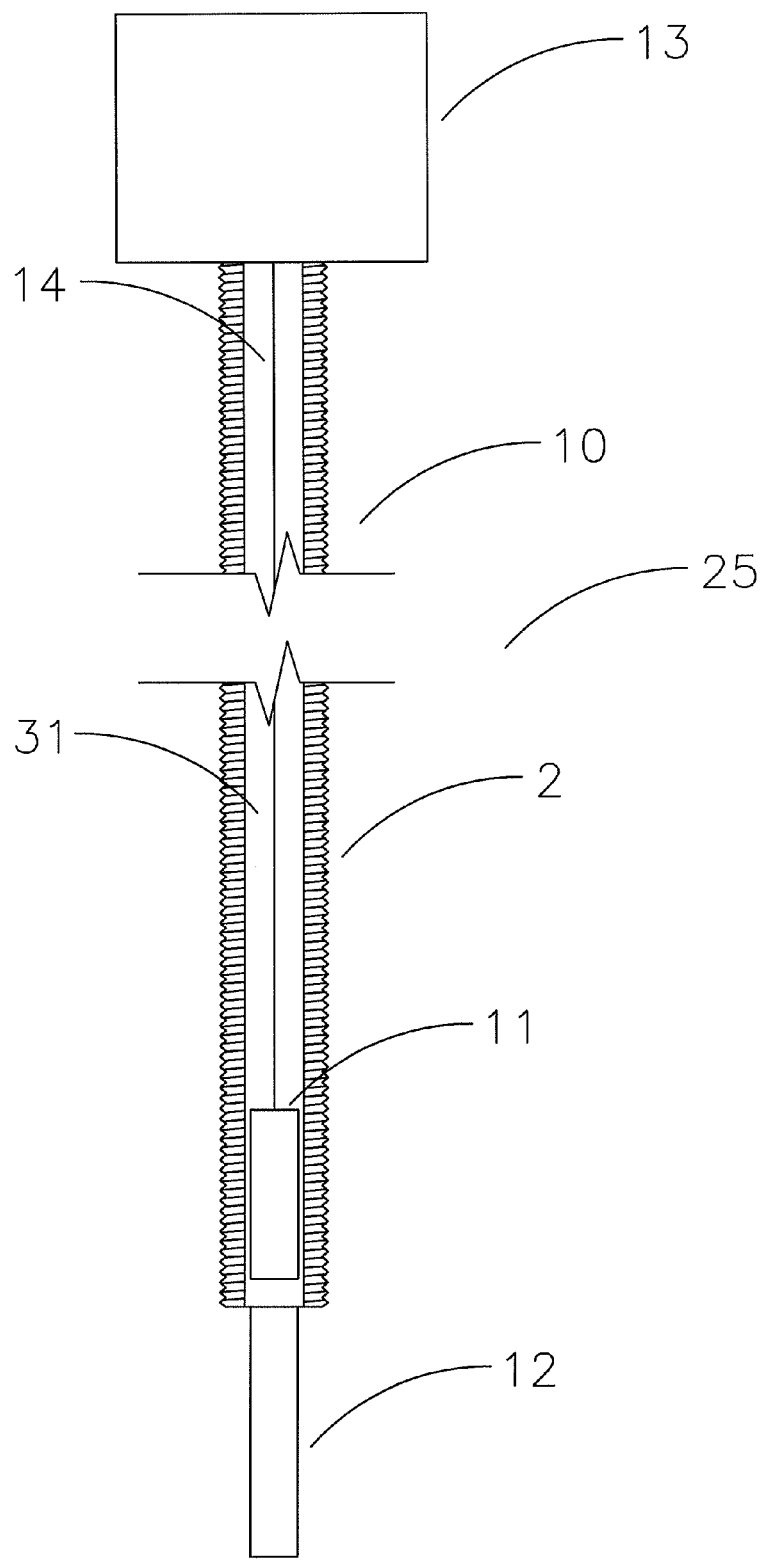
FIG. 3 is a side, partially cross-section al view of the threaded shaft of FIG. 1, illustrating regulator mounted thereon to its first end, a with pressure regulator mounted situated within said threaded shaft adjacent to its second end, a force transfer rod situated therebetween, and a membrane probe top in communication with said pressure regulator valve cartridge, said probe tip emanating from said second end of said threaded shaft.

Insertion assembly 25 can be utilized to perform a fluid sample extraction task when threaded probe shaft 2 is configured as shown in FIG. 3. A passage 31 provides fluid communication between regulator body 13 and pressure regulator valve cartridge 11, said passage 31 also houses force transfer rod 14 which provides mechanical communication between a pressure regulating diaphragm (not shown) located in regulator body 13 and the pressure regulator valve cartridge 11. In the preferred embodiment a phase separation membrane tip 12 filters solids and entrained liquids when the fluid to be sample is a gas.

Referring to the Figures, in use, pressurized fluid source 27, in this example, flowing process gas, engages the probe shaft 2, applying pressure to same which may result in vibrations or harmonic resonance 51. Because the probe shaft 2, however, is in effect isolated from housing 3 via elastomeric material or the like, those vibrations are effectively absorbed by said elastomeric material, as well as the thermoplastic material forming thread insert 4.

Figure 4:
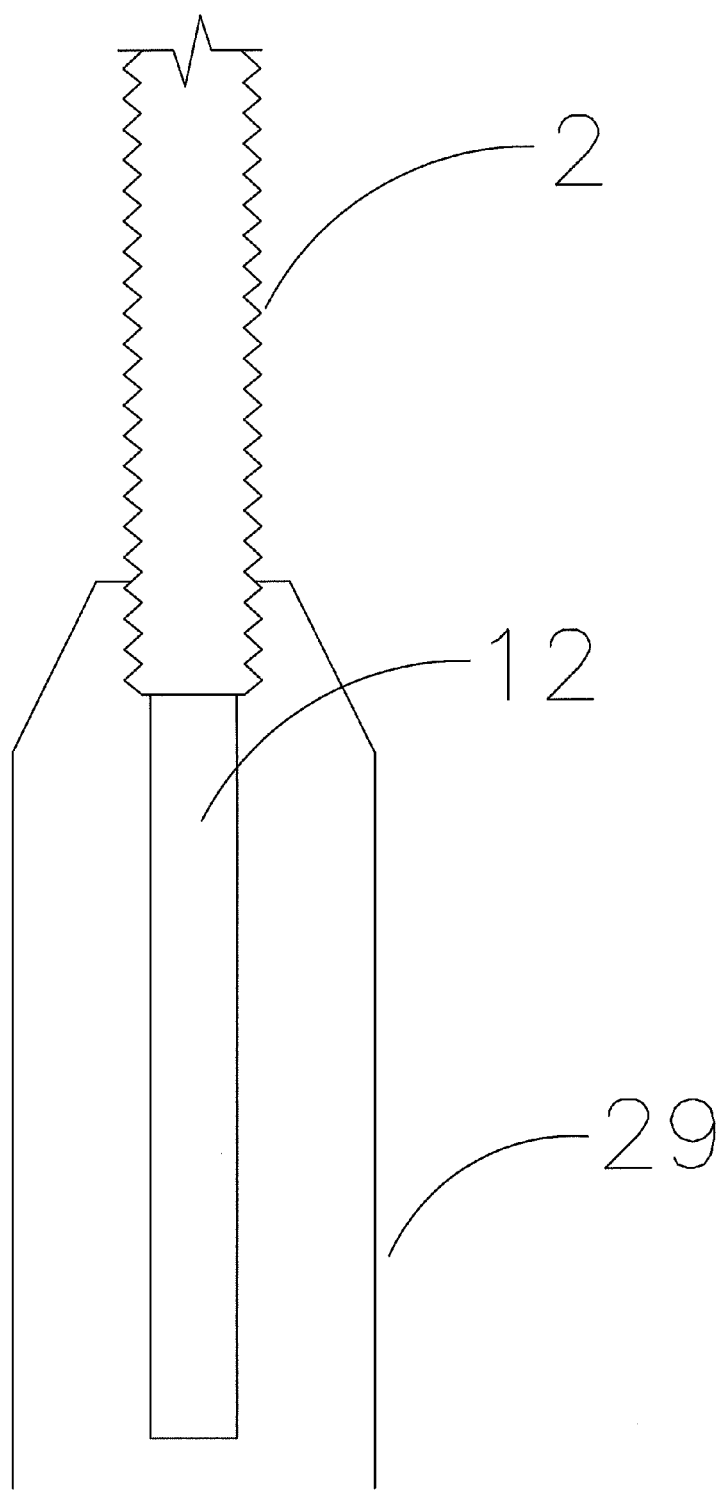
FIG. 4 is a side, cut-away view of the probe tip of FIG. 3, with a shroud situated thereabout.

With regard to the sealing properties of the present invention, in operation, gas filtered of solids and liquid by phase separation member tip 12, flows into pressure regulator valve cartridge wherein the pressure is regulated, said gas then flows into passage 31, around force transfer rod 14, to regulator body 13 wherein it exits from a port which is not shown. In a similar manner, threaded probe shaft 2 can be configured to extract a fluid sample without pressure regulation or membrane filtration. In cases wherein threaded probe shaft 2 is configured with a phase separation membrane tip a shroud 29, refer to FIG. 4, may be positioned around phase separation membrane tip 12 to protect said phase separation membrane tip 12 from damage from high fluid flow or entrained solids.

Figure 5:
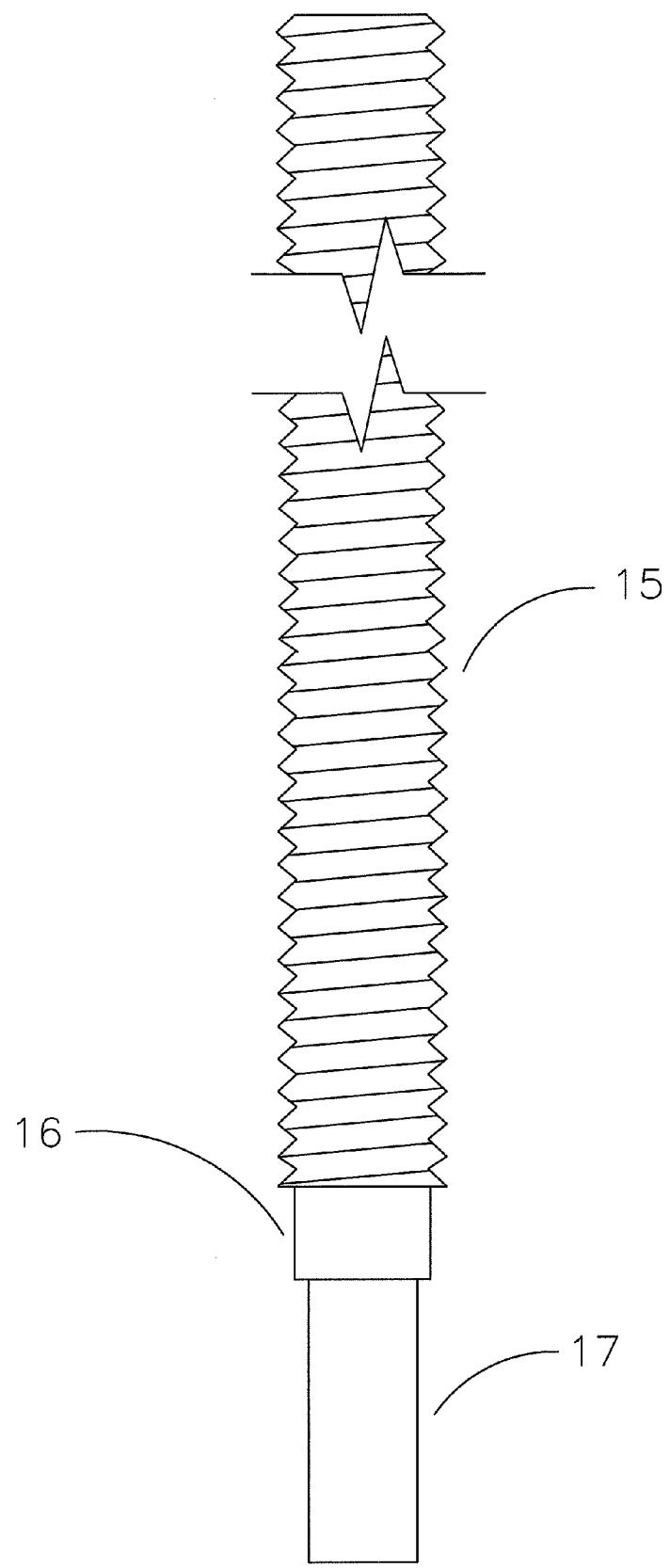
FIG. 5 is a side, close-up view of the probe tip of FIG. 1, but with a corrosion coupon mounted thereon.

In a second embodiment of the present invention threaded probe shaft 15 is configured to receive a corrosion coupon, refer to FIG. 5. In said second embodiment corrosion coupon adapter 16 provides a transition between probe adapted for insertion of corrosion coupon 15 and corrosion coupon 17. Said threaded probe shaft 15 adapted for insertion of corrosion coupon 17 does not require a fluid passage.

Figure 6:
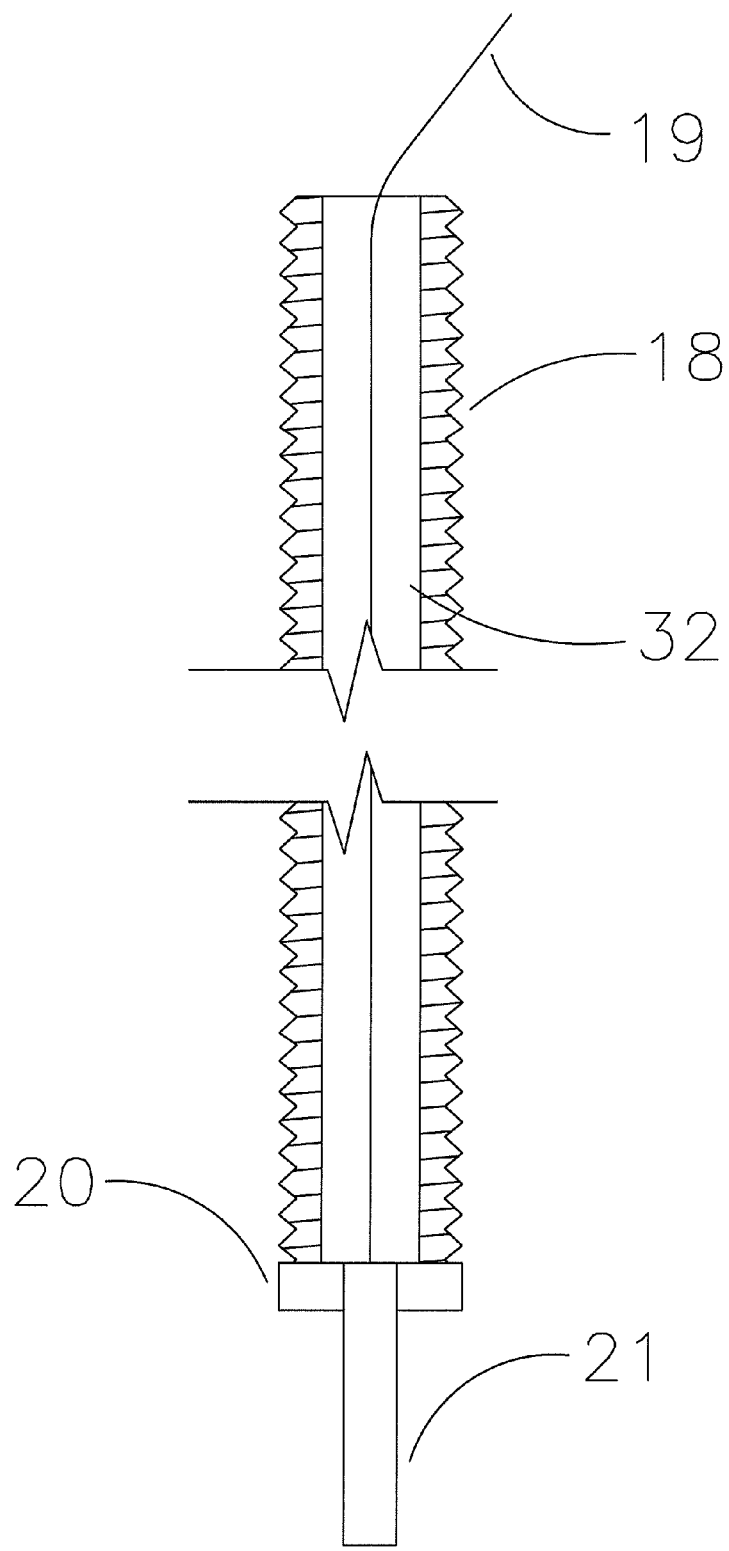
FIG. 6 is a side, close-up view of the probe tip of FIG. 1, but with a sensor mounted thereon, with a sensor cable running through the treaded probe shaft.

In a third embodiment of the present invention threaded probe shaft 18 is configured for mounting and insertion of sensors 21, refer to FIG. 6. In said third embodiment said probe shaft 18 has a passage 32 which houses sensor cable 19. Pressure seal 20 provides a fluid barrier between a pressurized fluid into which sensor 21 has been inserted and passage 32.

The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

What is claimed is:

1. An insertion assembly comprising:
   a housing having a passage formed therethrough having first and second ends, said first end of said passage formed to fluidly engage a pressurized fluid source;
   a first retention nut having a probe shaft passage formed therethrough, said first retention nut having an outer diameter formed to threadingly engage said inner diameter of said housing passage in the vicinity of second end of said housing passage;
   a second retention nut having a probe shaft passage formed therethrough, said second retention nut having an outer diameter formed to threadingly engage the said inner diameter of said housing passage;
   a packing gland situated between said first and second retention nuts;
   a threaded shaft having first and second ends, an outer diameter, and a length having a fluid passage formed therethrough, said threaded shaft extending through said probe shaft passages of said first and second retention nuts and through said first and second ends of said housing passage without contacting same, said threaded shaft forming a probe shaft;
   wherein said packing gland directly engages said outer diameter of said threaded shaft so as to form a fluid barrier about said outer diameter of said threaded shaft; and
   wherein said packing gland supports said probe shaft passage within said housing, so as to isolate said housing from said probe shaft.

2. The invention of claim 1 wherein said first end of said housing has NPT pipe threads formed at said first end of said passage.

3. The invention of claim 1 wherein said first end of said housing is formed for flanged mounting.

4. The invention of claim 1 wherein said packing gland is formed of layered, elastomeric split discs.

5. The invention of claim 1 wherein said packing gland is constructed from elastomeric material.

6. The invention of claim 5 wherein said packing gland is constructed from a plurality of layers.

7. The invention of claim 6 wherein the layer of said packing gland exposed to the process is impervious to said fluid in said pressurized fluid source.

8. The invention of claim 7 wherein said packing gland is formed to be adjustably compressible by adjusting said first or second retention nuts so as to provide a leak proof fluid barrier under varying conditions.

9. The invention of claim 1 wherein the said threaded shaft has a fluid passage through its axis.

10. The invention of claim 9 wherein said fluid passage is formed to facilitate the flow therethrough of a fluid sample from a pressurized fluid source.

11. The invention of claim 10 wherein said threaded shaft fluid passage has situated therein a pressure regulator valve cartridge in the vicinity of said first end of said threaded shaft, said second end of said threaded shaft has a regulator body associated therewith, and a force transfer rod engaging said pressure regulator valve cartridge with said regulator body, so as to provide mechanical communication between said regulator body and said pressure regulator valve cartridge to facilitate integral pressure control.

12. The invention of claim 10 wherein said fluid sample is filtered.

13. The invention of claim 12 wherein said filtration is by use of a phase separation membrane.

14. The invention of claim 1 wherein said threaded shaft is formed to facilitate the passage of objects therethrough to engage a pressurized fluid.

15. The invention of claim 14 wherein said object comprises a corrosion coupon.

16. The invention of claim 14 wherein said object comprises a sensor.

17. The invention of claim 16 wherein said sensor comprises a pressure sensor.

18. The invention of claim 16 wherein said sensor comprises a temperature sensor.

19. The invention of claim 14 wherein said object comprises a composition analyzer.

20. The invention of claim 14 wherein said object comprises a composition monitor.

21. The invention of claim 1 wherein there is further provided an insert in sliding engagement with said housing passage between said second retention nut and said first end of said housing, said insert having formed therethrough a threaded passage in threaded engagement with said threaded shaft.

22. The invention of claim 21 wherein said second retention nut is formed to lock said insert in place, so that said insert threadingly engages said threaded shaft to facilitate the repositioning of said threaded shaft through said housing by the axial rotation of said threaded shaft.

23. The invention of claim 22 wherein said insert is constructed from a plastic material.

24. The invention of claim 23 wherein said plastic material is Kevlar.

25. The invention of claim 1 wherein said insertion assembly is also comprised of a cleaning die or threaded nut threadingly engaging said threaded shaft between said insert and said first end of said housing.

26. The invention of claim 25 wherein said cleaning die or nut is adapted for restraining said threaded shaft in the event of thread failure.

27. The invention of claim 1 wherein there is further provided a valve situated between said first end of said housing and said fluid source container, said valve configured to selectively open to allow said first end of said threaded shaft to pass from said housing, through said open valve and into said pressurized fluid source container.

28. The invention of claim 21, wherein said insert is formed of a thermoplastic material so as to absorb vibration in said probe shaft.

29. The invention of claim 28, wherein said threads forming said probe shaft outer diameter are formed to facilitate fluid flow thereabout so as to aerodynamically stabilize the same, thereby dampening harmonic resonance in said probe shaft.

30. The invention of claim 28, wherein said packing gland supports said probe shaft so as to diminish vibrations present in said probe shaft, while isolating said housing from any vibrations present in said probe shaft.

31. The invention of claim 1, wherein said packing gland is formed to support said probe shaft so as diminish vibrations present in said probe shaft, while isolating said housing from any vibrations present in said probe shaft.

* * * * *